(12) United States Patent
Papa et al.

(10) Patent No.: US 11,236,289 B2
(45) Date of Patent: Feb. 1, 2022

(54) METHOD FOR THE PRODUCTION OF AN OZONIZED OLIVE OIL

(71) Applicant: Organicare LLC, Austin, TX (US)

(72) Inventors: Franco Papa, Lesa (IT); Renato Colognato, Ispra (IT)

(73) Assignee: Organicare, LLC, Austin, TX (US)

(*) Notice: Subject to any disclaimer, the term of this patent is extended or adjusted under 35 U.S.C. 154(b) by 0 days.

(21) Appl. No.: 16/772,516

(22) PCT Filed: Nov. 22, 2018

(86) PCT No.: PCT/IB2018/059205
§ 371 (c)(1),
(2) Date: Jun. 12, 2020

(87) PCT Pub. No.: WO2019/102387
PCT Pub. Date: May 31, 2019

(65) Prior Publication Data
US 2020/0385649 A1 Dec. 10, 2020

(30) Foreign Application Priority Data
Nov. 22, 2017 (IT) .................. 102017000133598

(51) Int. Cl.
*C11C 3/00* (2006.01)
*C07C 45/40* (2006.01)

(52) U.S. Cl.
CPC .............. *C11C 3/006* (2013.01); *C07C 45/40* (2013.01)

(58) Field of Classification Search
CPC ................................ C11C 3/006; C07C 45/40
See application file for complete search history.

(56) References Cited

U.S. PATENT DOCUMENTS

| | | | | |
|---|---|---|---|---|
| 2,865,937 A | * | 12/1958 | Maggiolo | C07C 55/08 554/133 |
| 3,504,038 A | * | 3/1970 | Beal | C07C 45/40 568/469 |
| 5,997,876 A | | 12/1999 | Shikhashvili et al. | |
| 2005/0008663 A1 | | 1/2005 | Lerma | |
| 2005/0010069 A1 | * | 1/2005 | Fitchett | B01J 19/247 568/959 |
| 2006/0074129 A1 | * | 4/2006 | Mirabal | A61P 31/00 514/547 |
| 2008/0045594 A1 | | 2/2008 | Piccirilli et al. | |

(Continued)

FOREIGN PATENT DOCUMENTS

| | | |
|---|---|---|
| EP | 2014295 | 1/2009 |
| EP | 2510912 | 10/2012 |
| WO | 2012168770 | 12/2012 |

OTHER PUBLICATIONS

Diaz, M.F. et al., Study of three systems ozonized coconut oil, 2005, Ozone: Science and Engineering, , 27, pp. 153-157 (Year: 2005).*

(Continued)

*Primary Examiner* — Yate' K Cutliff
(74) *Attorney, Agent, or Firm* — Kowert, Hood, Munyon, Rankin & Goetzel, P.C.; Gareth M. Sampson

(57) ABSTRACT

The present invention relates to a method for the production of an ozonized olive oil with a controlled degree of ozonization, wherein said method comprises at least one step of putting the olive oil into contact with ozone in the presence of water.

16 Claims, 3 Drawing Sheets

(56) References Cited

U.S. PATENT DOCUMENTS

2009/0035387 A1* 2/2009 Papa .................. B01J 10/002
424/613
2009/0291122 A1 11/2009 Vandeputte

OTHER PUBLICATIONS

Almeida, et al., "Ozonized Vegetable Oils and Therapeutic Properties: A Review". Orbital, The Electronic Journal of Chemistry, vol. 4, No. 4, Oct.-Dec. 2012, pp. 313-326.

Berenji, et al., "Comparing the Effect of Ozonized Olive Oil with Clotrimazole on Three Candida Species *C albiacans, C. Glabrata, C. Krusei*", E3 Journal of Microbiology Research, vol. 2(1), pp. 009-013, Jan. 2014.

Diaz, et al., "Comparative Study of Ozonized Olive Oil and Ozonized Sunflower Oil", J. Braz. Chem. Soc., vol. 17, No. 2, pp. 403-407, 2006.

Geweely, "Antifungal Activity of Ozonized Olive Oil (Oleozone)", International Journal of Agriculture & Biology, vol. 8, No. 5, 2006, pp. 670-675.

Gomez, et al., "Chemical Analysis of Ozonized Theobroma Fat", JAOCS, vol. 83, No. 11, 2006, pp. 943-946.

Kogawa, et al., Synthesis, Characterization, Thermal Behavior, and Biological Activity of Ozonides from Vegetable Oils, The Royal Society of Chemistry, 2013, pp. 1-13.

Kumar, et al. "Efficacy of Ozonized Olive Oil in the Management of Oral Lesions and Conditions: A Clinical Trial", Contemporary Clinical Dentistry, 2016, 11 pages.

Moureu, et al., "Ozonation of Sunflower Oils: Impact of Experiemental Conditions on the Composition and the Antibacterial Activity of Ozonized Oils", Chemistry and Physics of Lipids, vol. 186, Feb. 2015, pp. 79-85 (Abstract).

Tellez, et al., "Measurement of Peroxidic Species in Ozonized Sunflower Oil", The Journal of the International Ozone Association, vol. 28, Issue 3, 2006 (Abstract).

International Preliminary Report on Patentability for PCT/IB2018/052324 dated Oct. 8, 2019, 7 pages.

International Preliminary Report on Patentability for PCT/IB2018/059205 dated Mar. 5, 2020, 14 pages.

International Search Report for PCT/IB2018/052324 dated Jun. 20, 2018, 4 pages.

International Search Report for PCT/IB2018/059205 dated Mar. 21, 2019, 4 pages.

Written Opinion for PCT/IB2018/052324 dated Oct. 11, 2018, 6 pages.

Written Opinion for PCT/IB2018/059205 dated May 31, 2019, 6 pages.

* cited by examiner

METHOD FOR THE PRODUCTION OF AN OZONIZED OLIVE OIL

The present invention relates to a method for the production of an ozonized olive oil with a controlled degree of ozonization.

PRIOR ART

The clinical use of ozonized vegetable oils is broadly known in the art. The products of oxidation that are formed by reacting ozone with the fatty acids contained in vegetable oils have a germicidal, antimycotic and immunostimulating effect when the ozonized oils are applied topically.

By virtue also of their properties of stimulating tissue regeneration, ozonized vegetable oils can thus be used for the topical treatment of wounds, infected wounds in particular.

In order to facilitate the topical application of ozonized vegetable oils and prolong the presence of the product on the area to be treated, such oils are preferably marketed in the form of a gel or an extremely viscous liquid. Completely ozonized vegetable oils having a stable gel form can be simply produced by bubbling ozone inside a reactor in which liquid vegetable oil is placed in the absence of solvent, for example according to the method described in patent application EP2025740A1.

The peroxide value (PV) of an ozonized oil brought to complete ozonization is determined by the quantity and quality of the unsaturated fatty acids present, which give rise to different peroxidation reactions in the presence of ozone. The peroxidated products that are formed, for example peroxides, hydroperoxides and ozonides, are responsible for the wide spectrum of therapeutic action of ozonized oils.

The viscosity of the liquid, as well as the formation of a stable gel, increase with increases in the degree of ozonization of the oil, where the degree of ozonization is directly proportional to the time of contact between the ozone and the substrate. The ozonization process described in EP2025740A1 makes it possible to obtain solely ozonized olive oil which, as a stable gel, exhibits a pre-determined peroxide value, which substantially depends on the number and type of unsaturated fatty acids contained in the oil.

There is thus a felt need in this field to have a method for ozonizing olive oil which enables the preparation of an ozonized oil that is not only in the form of a stable gel and/or has an appropriate viscosity, but whose peroxide value can also be varied without influencing the physical state of the ozonized oil.

Vegetable oil ozonization processes are known in the art which start from emulsions of oil in water. In these systems, the water is generally present in a high amount relative to the oil: from 1 to 6 times the amount of oil and solvent together in U.S. Pat. No. 2,865,937 and about 2.7 times the amount of oil in U.S. Pat. No. 3,504,038.

However, such processes do not enable an ozonized oil in the form of a stable gel with a suitable peroxide value to be obtained.

Patent application US2006/0074129 discloses a method for obtaining ozonized oils with a peroxide value ranging from 200 to 1200 by bubbling ozone into an oil or a liquid fat to which 1-50 vol. % of water has been added. In the example embodiments, large amounts of water are used, 3 litres of water per 10 litres of oil, equal to about 23 vol. %, along with a high ratio between the gas flow rate and the volume of oil used (200 litres/h of gas consisting of an oxygen/ozone mixture per 10 litres of oil). The peroxide value of the ozonized oils produced in the examples varies between 600-800 units for sunflower oil and 1000-1200 units for *Theobroma* oil. Furthermore, the ozonized oils produced, despite having a variable peroxide value, have a low viscosity (less than 350 mPa·s for ozonized sunflower oil).

In this context, the principal object of the present invention is to propose a method for the production of ozonized oil with a controlled peroxide value, preferably in the form of a stable gel.

A further object of the present invention is to propose a method for the preparation of an ozonized oil which makes it possible to obtain the target peroxide value and/or viscosity value of the ozonized oil in a short time, using a limited amount of reagents per unit of volume of oil.

SUMMARY OF THE INVENTION

These and further objects, which will become more apparent in the course of the detailed description that follows, are achieved in accordance with the present invention, which, in a first aspect thereof, relates to a method for preparing an ozonized olive oil comprising:

(i) preparing a dispersion comprising olive oil and optionally, but preferably, water; and (ii) at least one step of bubbling a quantity Q1 of ozone into the dispersion and, optionally, adding water, wherein:
  in step (ii) the water is added in the liquid phase or vapour phase; and
  the total quantity of water added to the at least one olive oil in steps (i) and/or (ii) is approximately 0.5-15.0 vol. %.

In a further aspect, the present invention relates to an ozonized olive oil that is obtained/obtainable with the above-described method and characterized by at least one of the following properties:
  it is in the form of a stable gel, in which the change in the peroxide value $\Delta PV$ approximately 100.0, where $$\Delta PV = (PV_{t0} - PV_{t24})$$

wherein:
$PV_{t0}$=peroxide value measured at the end of step (b) and $PV_{t24}$=peroxide value measured at 24 months after the end of step (b); and/or
has a peroxide value PV approximately 2000 mEq $O_2$/Kg.

DETAILED DESCRIPTION OF THE INVENTION

Figure 1:
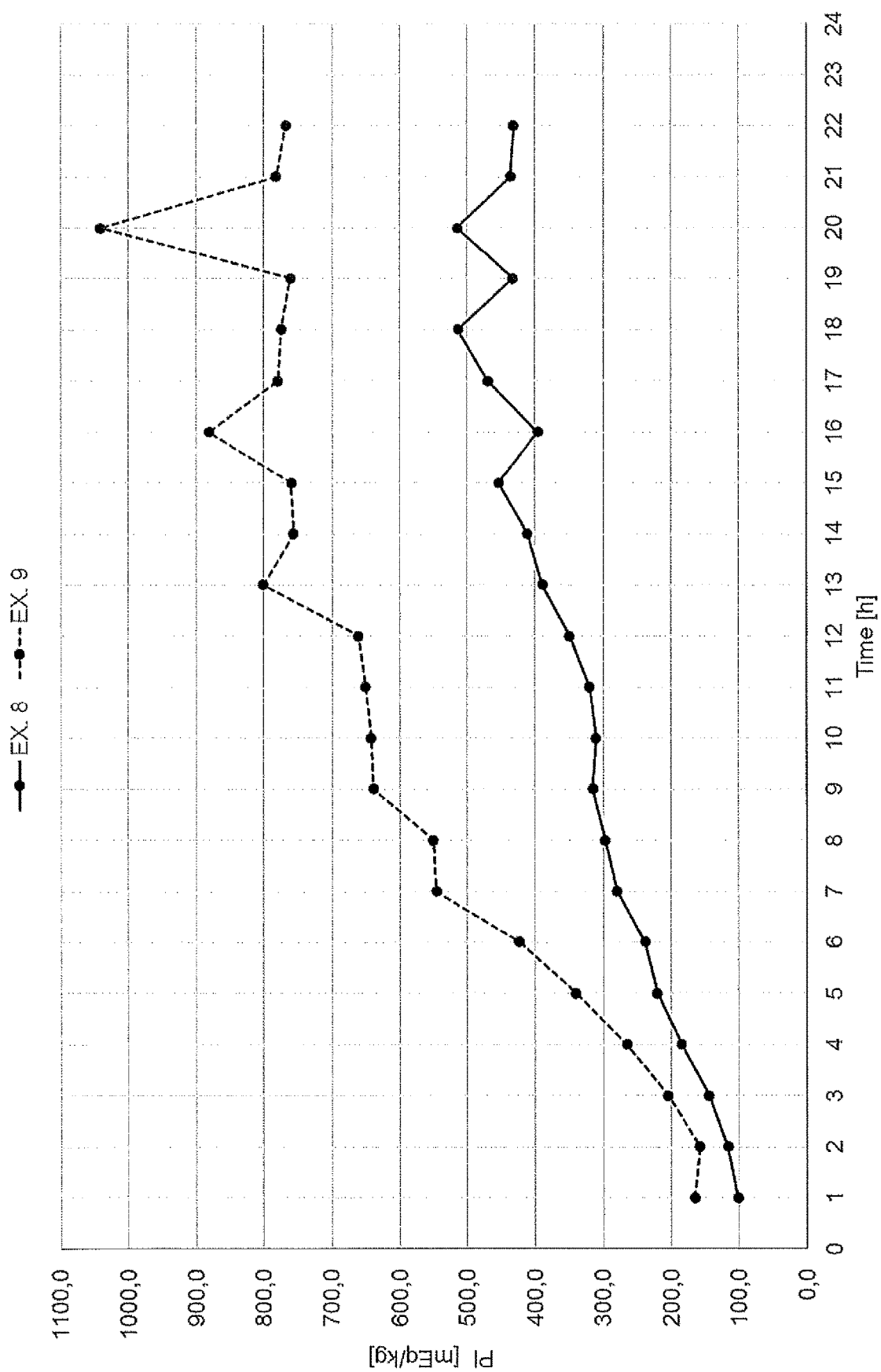
FIG. 1 shows a graph of the change in the peroxide value of the oils of examples 8 and 9, as a function of the reaction time.

In the context of the present invention, the term "dispersion" refers to a heterogeneous system consisting of a prevalent liquid phase (dispersing phase or continuous phase) in which a liquid phase that is immiscible with the dispersing phase is dispersed (dispersed phase). The drops constituting the dispersed phase can have dimensions that are greater than or equal to approximately $10^{-3}$ µm. In the context of the present invention, the term "emulsion" refers to a dispersion in which the drops constituting the dispersed phase have dimensions of approximately $10^{-3}$-1 µm.

In the context of the present invention, the term "W/O dispersion" or the term "W/O emulsion" refers, respectively, to a water-in-oil dispersion or emulsion, in which the oil constitutes the continuous phase and the water the dispersed phase.

In the context of the present invention, the term stable "dispersion (or emulsion)" refers to a dispersion (or emulsion) in which the drops constituting the dispersed phase do not give coalescence with the consequent formation of a continuous phase when the dispersion (or emulsion) is maintained at rest at approximately 25° C. for a time of approximately 5 minutes.

In the present description and in the appended claims, the term "vegetable oil" refers to a liquid mixture at 25° C. and 101.3 kPa mainly consisting of esterified lipids, generally obtained from fruits and seeds of oil-bearing plants.

In the context of the present invention, the terms "oleic acid", "linoleic acid" and more in general "fatty acid" refer, respectively, to the oleic, linoleic and fatty acids present in a vegetable oil in esterified form, preferably in the form of triglycerides. The term "free fatty acid" is used in the context of the present invention to indicate a non-esterified fatty acid.

In a first aspect, the present invention relates to a method for preparing an ozonized olive oil comprising:
  (i) preparing a dispersion comprising olive oil and optionally, but preferably, water; and
  (ii) at least one step of bubbling a quantity Q1 of ozone into the dispersion and, optionally, adding water, wherein:
    in step (ii) the water is optionally added in the liquid phase or vapour phase; and
    the total quantity of water added to the olive oil in steps (i) and/or (ii) is 0.5-15.0 vol. %.

The total quantity of water added to the olive oil in steps (i) and/or (ii) is expressed as a volume percent of the total volume of the dispersion.

The olive oil can comprise oleic acid (C18:1) and linoleic acid (C18:2) in a total amount that is greater than or equal to 35% by weight, wherein the total amount of oleic acid and linoleic acid is expressed as a sum of the percent amounts of the two fatty acids relative to the total amount of vegetable oils.

The olive oil can preferably be of biological origin and/or have an acid value less than or equal to approximately 2.0 mgKOH/g.

In a first embodiment, the method can comprise a step (i) of preparing a W/O dispersion comprising olive oil and the total quantity of water to be used in the method. According to this embodiment, the at least one step (ii) can be carried out using anhydrous ozone, in the absence of water vapour.

More specifically, the method for preparing an ozonized olive oil can comprise:
  (i.a) preparing a W/O dispersion comprising (or consisting of) olive oil and approximately 0.5-15.0 vol. % of water, preferably approximately 1.1-12.0 vol. %, more preferably approximately 1.1-10.0 vol. %, even more preferably approximately 1.5-8.0 vol. %; and
  (ii.a) at least a step of bubbling a quantity Q1 of ozone, preferably anhydrous ozone, into the W/O dispersion.

Step (i.a) can comprise adding the above-mentioned quantity of water, in the liquid phase, to the olive oil, and mixing the components with mechanical (e.g. stirrers) and/or physical (e.g. ultrasound) dispersing means normally used in the art to obtain preferably stable W/O dispersions.

According to one variant, step (i.a) can be carried out by mechanically dispersing water in the vegetable oils and subsequently treating the W/O dispersion with ultrasound.

According to one variant, step (i.a) can comprise:
  (i.a1) preparing a pre-dispersion, preferably a pre-emulsion, comprising a quantity Q2 of water and at least one vegetable oil, preferably at least one vegetable oil comprising oleic acid (C18:1) and linoleic acid (C18:2) in a total amount greater than or equal to approximately 35% by weight, so as to obtain a first dispersion, preferably a first emulsion; and (i.a2) mixing the first dispersion and olive oil so as to obtain a second W/O dispersion, preferably a second W/O emulsion, comprising approximately 0.5-15.0 vol. % of water, preferably 1.1-12.0 vol. %, more preferably 1.1-10.0 vol. %, even more preferably 1.5-8.0 vol. %.

A quantity Q1 of ozone, preferably anhydrous ozone, is subsequently bubbled into the W/O dispersion to obtain an ozonized olive oil.

In one embodiment, the quantity of water Q2 can be less than or equal to approximately 60 vol. %, preferably less than or equal to approximately 50 vol. %, more preferably approximately 30-50 vol. %, even more preferably approximately 40 vol. %, wherein the quantity Q2 is expressed as a volume of water relative to the total volume of the pre-dispersion (or pre-emulsion). The Applicant has surprisingly found that if the quantity Q2 of water pre-dispersed in the at least one vegetable oil is above 60 vol. %, when the pre-dispersion is added to the vegetable oil there will be a coalescence of the dispersed phase with the formation of a continuous aqueous phase which prejudices the optimal completion of the ozonization reaction (step (ii.a)).

The pre-dispersion step (i.a1) can comprise adding water to the vegetable oil using mechanical (e.g. stirrers) and/or physical (e.g. ultrasound) dispersion means normally used in the art in order to obtain preferably stable dispersions.

Step (i.a1) can comprise pre-dispersing the components with a mechanical stirrer at a speed of approximately 500-1500 rpm, preferably approximately 1000 rpm, until obtaining a stable pre-dispersion.

Optionally, the pre-dispersion can be further treated with ultrasound after mechanical dispersion.

In a further embodiment, the method for preparing an ozonized olive oil can comprise a step (i) of preparing a W/O dispersion comprising olive oil and a smaller quantity of water than the total quantity of water to be used in the method.

In this embodiment, the at least one step (ii) can be carried out by bubbling ozone and water vapour into the W/O dispersion or adding water in the liquid phase to the olive oil and bubbling ozone, preferably anhydrous ozone, into the dispersion, so that the total quantity of water added in step (i) and in step (ii) is approximately 0.5-15.0 vol. %. Therefore, in one embodiment the method can comprise:
  (i.b) preparing a W/O dispersion comprising olive oil and water; and
  (ii.b) bubbling a quantity Q1 of ozone into the W/O dispersion and adding water,
    wherein:
    in step (ii.b) the water is added in the liquid phase or vapour phase and
    the total quantity of water added in steps (i.b) and (ii.b) is 0.5-15.0 vol. %, preferably 1.1-12.0 vol. %, more preferably 1.1-10.0 vol. %, even more preferably 1.5-8.0 vol. %.

Step (i.b) can be carried out as previously described for step (i.a).

In one variant of this further embodiment, step (i.b) of the method according to the invention can comprise:

(i.b1) preparing a pre-dispersion, preferably a pre-emulsion, comprising a quantity Q2 of water and at least one vegetable oil, preferably at least one vegetable oil comprising oleic acid (C18:1) and linoleic acid (C18:2) in a total amount greater than or equal to approximately 35% by weight, thus obtaining a first dispersion; and (i.b2) mixing the first dispersion and olive oil, thus obtaining a second W/O dispersion wherein the total quantity of water added in steps (i.b1), (i.b2) and (ii.b) is approximately 0.5-15.0 vol. %, preferably approximately 1.1-12.0 vol. %, more preferably approximately 1.1-10.0 vol. %, even more preferably approximately 1.5-8.0 vol. %.

Steps (i.b1) and (i.b2) can be can be carried out as previously described for steps (i.a1) and (i.a2).

The method can comprise adding water in the liquid phase to the olive oil and bubbling ozone, preferably anhydrous ozone, into the W/O dispersion. According to this embodiment, the method can comprise adding approximately 20-30 vol. % of the total water in step (i.b) and the remaining approximately 70-80 vol. % of the total water, preferably divided into 2-6 aliquots, more preferably aliquots of an equal amount, in step (ii.b).

Given the same total quantity of water added and ozone used, this embodiment enables an ozonized olive oil with a higher peroxide value to be obtained. Advantageously, furthermore, the peroxide value increases in a more regular manner as the reaction time increases when part of the water is added in step (ii.b), enabling a better control of the properties of the product, in particular the peroxide value and viscosity.

In a further embodiment, the method can comprise adding the total quantity of water for carrying out the method exclusively in step (ii) in the form of water vapour.

According to this embodiment, the method for preparing an ozonized olive oil can comprise a quantity Q1 of ozone and water vapour in the olive oil, wherein the total quantity of water added to the olive oil is approximately 0.5-15.0 vol. %, preferably approximately 1.1-12.0 vol. %, more preferably approximately 1.1-10.0 vol. %, even more preferably approximately 1.5-8.0 vol. %.

In the different embodiments of the method described above:
- the total quantity of water added in step (i), in the sub-steps, if any, of step (i), and/or in steps and sub-steps (ii) is approximately 0.5-15.0 vol. %, preferably approximately 1.1-12.0 vol. %, more preferably approximately 1.1-10.0 vol. %, even more preferably approximately 1.5-8.0 vol. %; and/or
- the water can be purified water, preferably water for injection, more preferably sterile water for injection, as defined in the 12th ed. of the Official Pharmacopeia of the Italian Republic; and/or
- the at least one vegetable oil of steps (i.a1) and/or (i.b1) can comprise a total of approximately 35-85% by weight, preferably approximately 50-80% by weight, more preferably approximately 55-75% by weight, of oleic acid (C18:1) and linoleic acid (C18:2); and/or
- the at least one vegetable oil can be selected from olive oil, olive pomace oil, peanut oil, corn oil, sunflower oil, rapeseed oil, sesame oil, rice oil, wheat germ oil, hemp seed oil, soybean oil, linseed oil, almond oil, neem oil, hazelnut oil, grapeseed oil, pumpkin seed oil and mixtures thereof, preferably the at least one vegetable oil can be olive oil, i.e. an oil deriving exclusively from the fruits of olive trees; and/or
- the quantity of ozone Q1 can be less than or equal to approximately 10.0 l/h of ozone per litre of oil, preferably less than or equal to approximately 7.5 l/h, more preferably approximately 1.0-7.5 l/h, even more preferably approximately 1.1-7.0 l/h, even more preferably approximately 1.5-6.5 l/h. In a further preferred variant, the quantity Q1 can be approximately 2.0-4.0 l/h of ozone per litre of oil; and/or
- at least one of steps (i.a), (i.a1), (i.a2), (i.b1) and (i.b2), preferably all of said steps, can be carried out at a temperature of approximately 20-25° C. and/or at a pressure of approximately 101.3 kPa; and/or
- the dispersion of at least one of steps (i.a), (i.a1), (i.a2), (i.b1) and (i.b2), preferably of all of said steps, can be a stable dispersion, it can preferably be an emulsion, even more preferably it can be a stable emulsion.

Because of its great instability, ozone is generally produced in situ by means of ozone generators known in the art, from a supply gas consisting of air or pure oxygen. The main methods for producing ozone are irradiation of the gas flow with UV light and corona discharge. In the method of the invention, an ozone generator that employs corona discharge can preferably be used.

Advantageously, before the supply gas reaches the ozone generator, said gas can be conveyed to at least one drying unit to reduce the quantity of water present in the gas itself, thus producing a dried supply gas. The presence of water in the supply gas significantly reduces the capacity of an ozone generator.

In a preferred embodiment, the dried supply gas flowing to the ozone generator can be dry air with a dew point less than or equal to approximately −50° C., preferably less than or equal to approximately −50° C. and greater than or equal to approximately −100° C.

In one embodiment, the ozone generator supplied with dry air as described above can produce a flow of dry air with an ozone concentration of approximately 1-15 vol. %, preferably approximately 3 vol. %, relative to the total volume of dry air.

When carrying out the method comprises bubbling water vapour and ozone, the flow of ozone can be humidified downstream of the ozonizer by means of humidification devices which are in themselves known in the art. Alternatively, the ozone can be supplied to step (ii) as dry ozone and the water vapour as an additional flow on its own.

The method can be carried out in a system comprising at least one bubble column reactor of the type normally employed for gas-liquid reactions. Such reactors are in themselves known in the art and therefore they are not further described in detail.

Since the ozonization reaction of a vegetable oil is exothermal, the at least one step of bubbling ozone can preferably be carried out under conditions of cooling in order to prevent an uncontrolled temperature increase in the reaction environment from causing deterioration of the oil or triggering combustion reactions.

In the context of the present disclosure, the expression "under conditions of cooling" refers to conditions in which the reaction heat generated by the ozonization of the vegetable oils is removed from the reaction environment.

Therefore, the bubble column reactor in which the at least one step of bubbling ozone can be carried out can comprise an external cooling compartment (or jacket), of the type known in the art, in which a cooling fluid circulates, generally water or mineral or silicone oil.

The temperature of the cooling fluid supplied to the reactor jacket can be approximately 15-25° C., preferably approximately 18°–22° C., the temperature being measured at a pressure of approximately 101.3 kPa.

In one embodiment, the at least one step of bubbling ozone can be carried out at a temperature less than or equal to approximately 35° C., preferably less than or equal to approximately 30° C., more preferably approximately 20-30° C.

The at least one step of bubbling ozone can be carried out at ambient pressure or, preferably, under vacuum, at a pressure preferably less than or equal to approximately 51 kPa.

The at least one step of bubbling ozone can have a variable duration.

In one embodiment, said step can be carried out until obtaining an ozonized oil in the form of a gel. In one embodiment, the at least one step of bubbling ozone can be carried out until obtaining an ozonized olive oil in the form of a stable gel, in which the change in the peroxide value $\Delta PV$ is less than or equal to approximately 100.0, preferably 70-90, where $$\Delta PV = (PV_{t0} - PV_{t24})$$

wherein:
$PV_{t0}$=peroxide value measured at the end of the at least one ozonization step and
$PV_{t24}$=peroxide value measured at 24 months after the end of the at least one ozonization step.

In one embodiment, the at least one step of bubbling ozone can be carried out until obtaining an ozonized oil with a peroxide value $PV_{t0}$ less than or equal to approximately 2000 mEq $O_2$/Kg, preferably approximately 350-2000 mEq $O_2$/Kg, more preferably approximately 350-1000 mEq $O_2$/Kg, even more preferably approximately 400-800 mEq $O_2$/Kg.

The at least one step of bubbling ozone can be carried out until obtaining an ozonized oil in the form of a stable gel with a $PV_{t0}$ as specified above.

The method according to the invention can comprise at least one step (ii) lasting approximately 14-24 hours, preferably approximately 18-24 hours, at the end of which the ozonized oil obtained can have at least one, preferably all, of the characteristics described above.

At the end of the at least one step of bubbling ozone, the flow of ozone can be interrupted and the ozonized vegetable oil removed from the reaction environment.

Alternatively, in order to obtain an ozonized vegetable oil with the desired characteristics, the method according to the invention can comprise a further step selected from:
(1) bubbling oxygen into the ozonized oil; and
(2) dispersing 0.5-15.0 vol. % of water in the ozonized vegetable oil.

The method according to the invention enables an ozonized vegetable oil with a controlled viscosity and peroxide value to be obtained, wherein said oil is preferably in the form of a stable gel.

It has been surprisingly found that, by appropriately modifying the conditions under which the at least one step (ii) is carried out within the operating parameters described above, it is possible to obtain an ozonized vegetable oil in the form of a stable gel and with high values of $PV_{t0}$ in a short time, i.e. considerably reducing the duration of the at least one step of bubbling ozone compared to the ozonization processes normally used in the art.

A further advantage of the ozonization method according to the invention lies in the fact that for the same $PV_{t0}$ of the ozonized oil a smaller amount of reagent is used than in the ozonization processes known in the art.

In a further aspect, the present invention relates to an ozonized olive oil obtained/obtainable with the method described above and characterized by at least one of the following properties:
it is in the form of a stable gel, in which the change in the peroxide value $\Delta PV$ is less than or equal to approximately 100.0, preferably 70-90, where $$\Delta PV = (PV_{t0} - PV_{t24})$$

wherein:
$PV_{t0}$=peroxide value measured at the end of step (b) and
$PV_{t24}$=peroxide value measured at 24 months after the end of step (b); and/or
it has a peroxide value $PV_{t0}$ less than or equal to approximately 2000 mEq $O_2$/Kg, preferably approximately 350-2000 mEq $O_2$/Kg, more preferably approximately 350-1000 mEq $O_2$/Kg, even more preferably approximately 400-800 mEq $O_2$/Kg.

The ozonized olive oil obtained/obtainable with the method described above has demonstrated bactericidal and/or antimycotic activity and can therefore have application in the treatment, preferably the topical treatment, of infections in humans and animals caused by bacteria and/or fungi.

Measurement Methods

Amount of oleic and linoleic acid: the percentage of fatty acids is determined by gas-liquid chromatography (GLC).

Acid value: the acid value is quantitatively determined using method ISO 660-2009

Peroxide value: iodometric titration with sodium thiosulphate of the iodine liberated by the reaction of the peroxides with potassium iodide (compliant with AOAC method No. 28.022). Apparatus: Mettler Toledo G20 titrator provided with an internal burette and DMi147-SC combined electrode (platinum—pH) and LabX® titration software. Titrating solution: sodium thiosulphate 0.1N (EXAXOL, Italy). Prepare a solution ("Sol.A") by mixing glacial acetic acid (#Cat. 33209, SIGMA Aldrich) and chloroform (#Cat. 132950-1L, SIGMA Aldrich) in a proportion of 3:2 v/v, under gentle stirring. Before taking the measurement, remove the electrode from the liquid it is preserved in and wash the electrode with deionised water for a few seconds. Weigh about 4 g of potassium iodide (#Cat. 30315, SIGMA Aldrich) into the beaker of the titrator; add 30 ml of "Sol.A" under stirring. Set the timer of the instrument to 4 minutes and start it, maintaining the solution under stirring. After 3 min. and 35" have elapsed, add 25 ml of deionised water to the solution and proceed with the automatic determination of the blank value (in the absence of the sample) with sodium thiosulphate. The blank determination makes it possible to calculate the relative error in the peroxide value due to changes in potential caused by the presence of any impurities in the reagents. The value in mmol of the titrant used for blank determination is memorised by the instrument as B[1]. To determine the peroxide value of the sample, exactly weigh about 2 g of sample into the beaker of the titrator, recording the amount of sample weighed (p) on the instrument, add 30 ml of "Sol.A" and stir until the sample is completely dissolved. Add about 4 g of KI to the solution to be titrated, set the timer of the instrument to 4 minutes and start it, maintaining the solution under stirring. After 3 min. and 35" have elapsed, add 25 ml of deionised water to the solution and proceed with the automatic titration of the iodine liberated from the sample with sodium thiosulphate. The result of the titration is positive if the instrument is able to record a minimum of 11 points on which to build the curve mapping the changes in potential and identify the curve inflection point. The instrument directly provides the peroxide value in meq/Kg $O_2$. The peroxide value is calculated as the arithmetic mean of three measurements performed on the same sample. Wash the electrode with chloroform between measurements.

Examples 1-3 and Comparative Example 4

For examples 1 and 2, 500 ml of a first W/O dispersion were prepared in a 1000 ml beaker by dispersing a quantity Q1 of purified water (Italian Official Pharmacopeia) with suitable amounts of organic olive oil having the characteristics shown in Table 1. The dispersion was mechanically stirred for approximately 1.5 min. at a speed of 1000 rpm. and a pale yellow milky W/O emulsion was obtained.

In example 3, the quantity of water Q2 was dispersed directly in the olive oil under mechanical stirring, without pre-mixing.

Table 2 shows the quantities Q1 and Q2 of water used in the different examples.

The emulsion was added to 4.5 l of the same organic olive oil, previously placed in bubble column reactor provided with a water-cooled jacket. The temperature of the cooling fluid was set at approximately 18° C.

A flow of dry air containing approximately 3 vol. % of ozone was bubbled into the oil at a flow rate of approximately 78 l/h per litre of oil (about 2.3 l/h of ozone per litre of oil).

The temperature of the reaction environment was kept below 30°–31° C. thanks to the cooling fluid.

Three samples of oil were taken from the reactor at the end of the reaction, 24 hours after the start of bubbling and the PV was determined for each sample. The PV shown in Table 2 was obtained as a mean of the values measured for three samples.

At the end of ozonization, the ozonized oil was in the form of an amber yellow gel.

TABLE 1 mean physicochemical characteristics of the olive oil

| Oleic acid (C18:1) | | 56-85% |
|---|---|---|
| Linoleic acid (C18:2) | | 3.5-20% |
| density | (25° C./101.3 kPa) | approx. 0.913 |
| acid value | mg KOH/g | ≤1.16 |
| PV | mEq $O_2$/Kg | ≤20 |
| unsaponifiable | | ≤2% |

TABLE 2

| | | Ex. 1 | Ex. 2 | Ex. 3 | Cp. Ex. 4 |
|---|---|---|---|---|---|
| | | Pre-emulsion | | | |
| $H_2O$ | ml | 100 | 175 | / | / |
| oil | ml | 400 | 325 | / | / |
| Q1 | (vol. %) | 20.0 | 35.0 | / | / |
| Q2 | (vol. %) | 2.0 | 3.5 | 10.0 | / |
| PV | mEq $O_2$/Kg | 600 | 990 | 1862 | 199 |

In a sample of ozonized oil product in example 2, a determination was made of the residual free water, which amounted to 0.266 at about 25° C. This value was wholly comparable to the value obtained in the sample of the comparative example 4, which showed to have a water content of 0.235 at about 25° C.

Comparative Example 5

500 ml of a first W/O dispersion were prepared in a 1000 ml beaker by dispersing 400 ml of purified water (Italian Official Pharmacopeia) in 100 ml of organic olive oil having the characteristics shown in Table 1. The dispersion was mechanically stirred for approximately 1.5 min. at a speed of 1000 rpm. and a pale yellow milky W/O emulsion was obtained.

The emulsion was added to 9.5 l of the same organic olive oil, previously placed in bubble column reactor provided with a water-cooled jacket. The temperature of the cooling fluid was set at approximately 18° C.

A flow of dry air containing approximately 3 vol. % of ozone was bubbled into the oil at a flow rate of approximately 78 l/h per litre of oil (about 2.3 l/h of ozone per litre of oil).

During bubbling, coalescence of the dispersed water occurred, with the formation of bubbles that precipitated onto the bottom of the reactor. At the end of the reaction, the determination of the peroxide value obtained showed a level of approximately 200, a parameter clearly indicative of a reduced and insufficient peroxidation of the fatty acids.

Example 6

500 ml of a first W/O dispersion were prepared in a 1000 ml beaker by dispersing 175 ml of purified water (Italian Official Pharmacopeia) in 325 ml of organic olive oil having the characteristics shown in Table 1. The dispersion was mechanically stirred for approximately 1.5 min. at a speed of 1000 rpm. and a pale yellow milky W/O emulsion was obtained.

The emulsion was added to 2.5 l of the same organic olive oil, previously placed in bubble column reactor provided with a water-cooled jacket. The temperature of the cooling fluid was set at approximately 18° C.

A flow of dry air containing approximately 3 vol. % of ozone was bubbled into the oil at a flow rate of approximately 312 l/h per litre of oil (about 9.4 l/h of ozone per litre of oil).

The temperature of the reaction environment was kept below 30°–31° C. thanks to the cooling fluid.

Three samples of oil were taken from the reactor 3, 8 and 24 hours after the start of the ozonization reaction and the PV was determined for each sample. The PV shown in Table 3 was obtained as a mean of the values measured for three samples.

At the end of the ozonization (24 h), the ozonized oil was in the form of an amber yellow gel.

TABLE 3

| | PV (mEq $O_2$/Kg) |
|---|---|
| t = 3 | 650 |
| t = 8 | 920 |
| t = 24 | 1190 |

Example of Application 7

500 ml of a first W/O dispersion were prepared in a 1000 ml beaker by dispersing 110 ml of purified water (Italian Official Pharmacopeia) in 390 ml of organic olive oil having the characteristics shown in Table 1. The dispersion was mechanically stirred for approximately 1.5 min. at a speed of 1000 rpm. and a pale yellow milky W/O emulsion was obtained.

The emulsion was added to 9.5 l of the same organic olive oil, previously placed in bubble column reactor provided with a water-cooled jacket. The temperature of the cooling fluid was set at approximately 18° C.

A flow of dry air containing approximately 3 vol. % of ozone was bubbled into the oil at a flow rate of approximately 78 l/h per litre of oil (about 2.3 l/h of ozone per litre of oil).

The temperature of the reaction environment was kept below 30°–31° C. thanks to the cooling fluid.

Three samples of oil were taken from the reactor at the end of the reaction, 24 hours after the start of the bubbling, and a PV of approximately 460 mEq $O_2$/Kg was determined as the mean of the values measured for three samples.

At the end of ozonization, the ozonized oil was in the form of an amber yellow gel.

The product obtained was tested to verify its effectiveness in inhibiting bacterial and/or fungal proliferation in accordance with the procedures of standard UNI EN 20645.

TABLE 4 inhibition of bacterial proliferation

| Strain | time | reduction in microbial growth | inhibition halo |
|---|---|---|---|
| Staphylococcus aureus | 4 h | >99% | 8 mm |
| (ATCC 6538) | 24 h | >99% | 10 mm |
|  | 48 h | >99% | 10 mm |
| Pseudomonas aeruginosa | 4 h | >99% | 7.5 mm |
| (ATCC 9027) | 24 h | >99% | 10.5 mm |
|  | 48 h | >99% | 10.5 mm |
| Staphylococcus epidermis | 4 h | >99% | 12 mm |
| (ATCC 12228) | 24 h | >99% | 15 mm |
|  | 48 h | >99% | 15 mm |

TABLE 5 inhibition of fungal growth

| Strain | time | Conc. of Inoculum (CFU/g) |
|---|---|---|
| Candida albicans | 15 h | ND |
| (ATCC 10231) | 30 h | <100 |
| 6.5 × 10⁵ CFU/g | 240 h | <100 |
| Aspergillus brasiliensis | 15 h | nd |
| (ATCC 16404) | 30 h | 1.2 × 10⁵ |
| 3.0 × 10⁵ CFU/g | 240 h | <100 |

Examples 8-11

The quantity of purified water (Italian Official Pharmacopeia) shown in table 6 was added to an olive oil in a bubble column reactor with a cooling jacket, the water being pre-emulsified in a suitable amount of oil. In examples 8 and 9, all of the water was added at the beginning of the reaction, before starting to bubble the ozone. In examples 10 and 11, part of the water was added before ozonization began and part once the reaction had begun, as indicated in table 6.

A flow of dry air containing approximately 3 vol. % of ozone was bubbled into the oil. The temperature of the reactor cooling fluid was set at approximately 18° C. The temperature of the reaction environment was kept below 30°–31° C. thanks to the cooling fluid.

Figure 2:
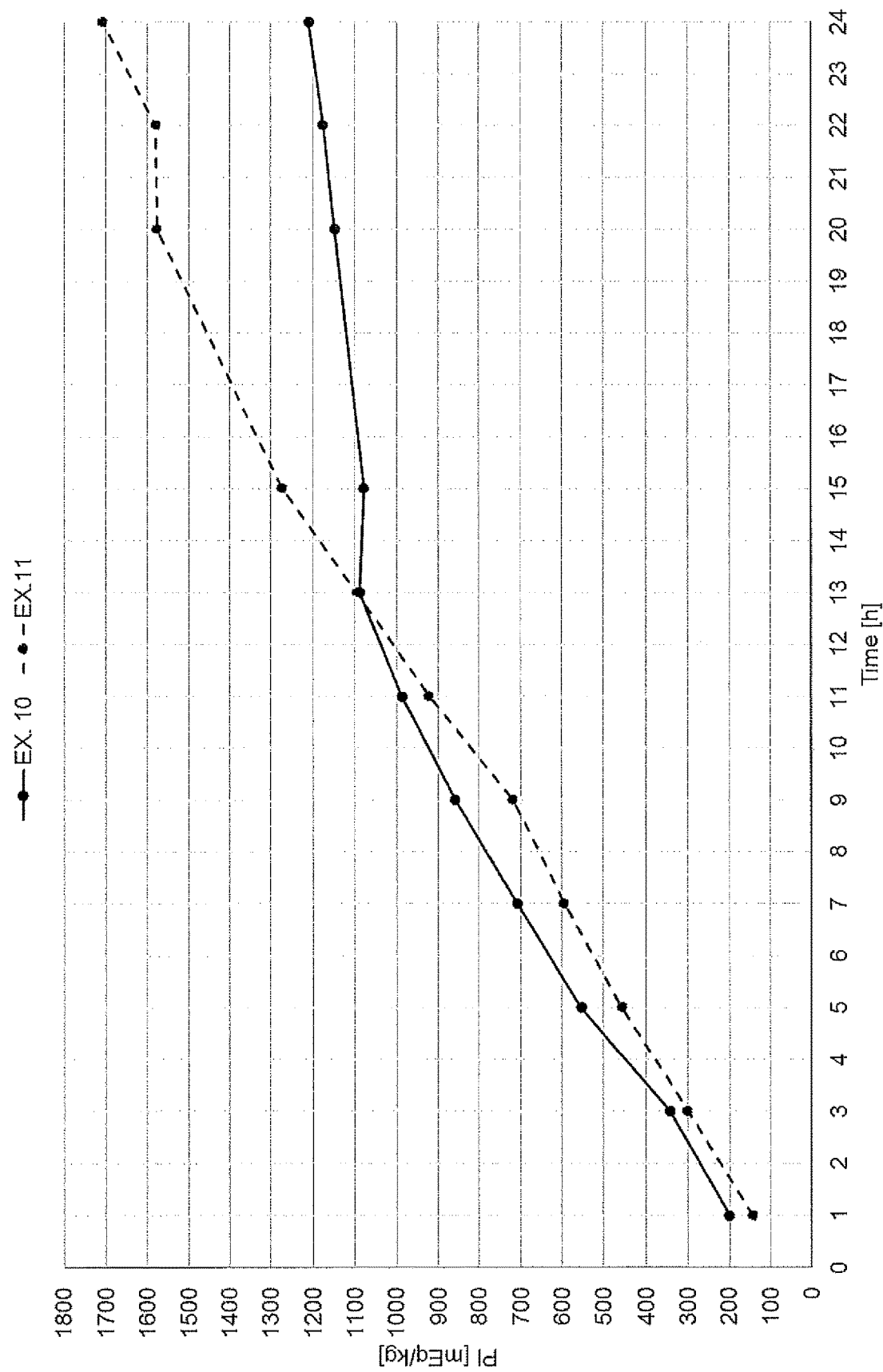
FIG. 2 shows a graph of the change in the peroxide value, as a function of the reaction time, for the ozonized oils in examples 10 and 11.

Samples of oil were taken from the reactor at different times during the ozonization reaction and at the end of the reaction, approximately 22/24 hours after the start of bubbling, and the PV was determined for each sample. The change in the peroxide value of the oils of examples 8-11, as a function of the reaction time, is shown in FIGS. 1 and 2.

Figure 3:
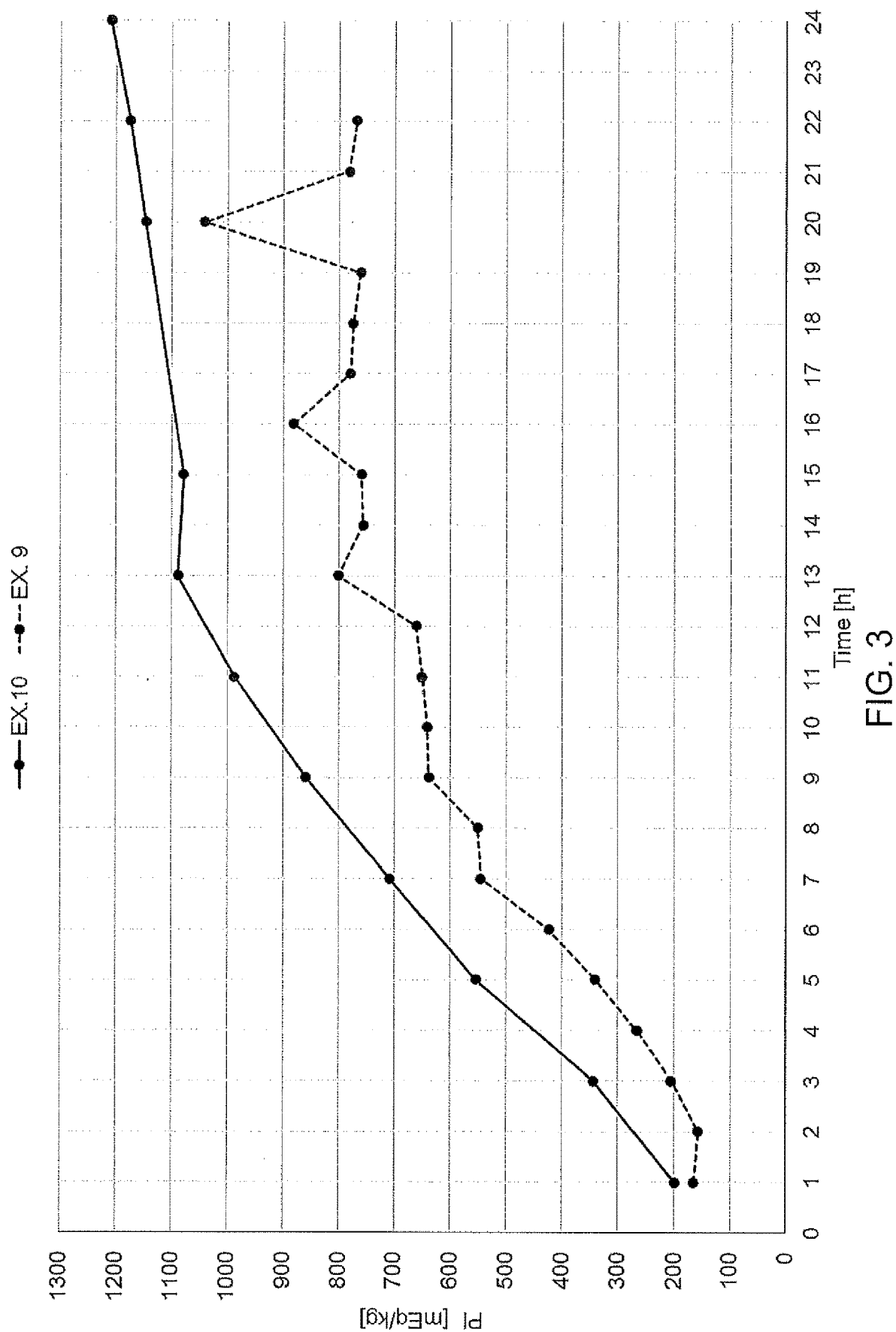
FIG. 3 shows a comparison between the change in PV, as a function of the reaction time, for examples 9 and 10.

FIG. 3 shows a comparison between the change in the PV, as a function of the reaction time, for examples 9 and 10.

TABLE 6

|  |  | Ex. 8 | Ex. 9 | Ex. 10 | Ex. 11 |
|---|---|---|---|---|---|
| Qty. of oil |  | 1 | 5 | 10 | 5 |
| Flow of $O_2/O_3$ mixture | lpm | 7 | 14 | 7 | 7 |
| Current | A | 7 | 14 | 7 | 7 |
| Total $H_2O$ | (vol. %) | 1.0 | 2.0 | 2.0 | 4.0 |
| time of introduction of $H_2O$ |  |  |  |  |  |
| t = 0 |  | 1.0% | 2.0% | 0.5% | 1.0% |
| t = 1 h |  | / | / | 0.5% | 1.0% |
| t = 3 h |  | / | / | 0.5% | 1.0% |
| t = 7 h |  | / | / | 0.5% | 1.0% |

The invention claimed is:

1. A method for preparing ozonized olive oil comprising:
   (i) preparing a pre-dispersion composition comprising a quantity of water (Q2) dispersed in a vegetable oil, wherein the quantity Q2 is expressed as a percentage calculated by dividing the volume of water used in the pre-dispersion composition by the total volume of the pre-dispersion composition and multiplying by 100, and wherein Q2 is from 35% to 60%;
   (ii) mixing the pre-dispersion composition with olive oil, wherein the amount of the pre-dispersion composition added to the olive oil is such that a dispersion of water in olive oil is obtained comprising 0.5 to 15 of water, wherein this percentage is calculated by dividing the volume of water used in the pre-dispersion composition by the total volume of the dispersion of water in olive oil and multiplying by 100; and
   (iii) bubbling a quantity Q1 of ozone into the dispersion of water in olive oil to form an ozonized olive oil.

2. The method according to claim 1, wherein the olive oil has an acid value less than or equal to 2.0 mgKOH/g.

3. The method according to claim 1, wherein the ozone is anhydrous ozone.

4. The method according to claim 1, wherein the vegetable oil comprises 35-85% by weight of oleic acid (C18:1) and linoleic acid (C18:2).

5. The method according to claim 1, wherein said at least one vegetable oil is selected from the group consisting of olive oil, olive pomace oil, peanut oil, corn oil, sunflower oil, rapeseed oil, sesame oil rice oil, wheat germ oil, hemp seed oil, soybean oil, linseed oil, almond oil, neem oil, hazelnut oil, grapeseed oil, pumpkin seed oil and mixtures thereof.

6. The method according to claim 1, wherein the quantity of ozone Q1 is less than or equal to 10.0 l/h of ozone per litre of oil.

7. The method according to claim 1, wherein bubbling ozone into the dispersion of water in olive oil is carried out under conditions of cooling, such that the dispersion of water in olive oil is kept at a temperature less than or equal to 35° C.

8. A method for preparing ozonized olive oil comprising:
   (i) preparing an initial dispersion of water in olive oil, wherein the step (i) comprises:

preparing a pre-dispersion composition comprising water dispersed in vegetable oil, the vegetable oil comprising oleic acid (C18:1) and linoleic acid (C18:2), wherein the total amount of water (Q2) in the pre-dispersion has a value of 35-60% by volume relative to the total volume of the pre-dispersion; and mixing the pre-dispersion composition with olive oil to obtain the initial dispersion; and (ii) bubbling a quantity Q1 of ozone and water into the initial dispersion of water in olive oil to form the ozonized olive oil;

wherein the total amount of water added during steps (i) and (ii) is such that the amount of water in the ozonized olive oil is 0.5 to 15% by volume.

9. The method according to claim 8, wherein the water added while bubbling ozone into the initial dispersion is added in a liquid phase.

10. The method according to claim 8, wherein the water added while bubbling ozone into the initial dispersion is added in the vapour phase.

11. The method according to claim 8, wherein, during step (ii), the ozone is anhydrous ozone, and the water is added in a liquid phase.

12. The method according to claim 8, wherein 20 to 30 vol. % of the total amount of water is added during step (i).

13. The method according to claim 8, wherein the water added during step (ii) is added in separate aliquots.

14. The method according to claim 8, wherein the vegetable oil comprises 35-85% by weight of oleic acid (C18:1) and linoleic acid (C18:2).

15. The method according to claim 8, wherein the quantity of Q1 is less than or equal to 10.0 l/h of ozone per litre of oil.

16. The method according to claim 8, wherein bubbling ozone into the initial dispersion is carried out under conditions of cooling such that the initial dispersion is kept at a temperature less than or equal to 35° C.

* * * * *

UNITED STATES PATENT AND TRADEMARK OFFICE
CERTIFICATE OF CORRECTION

PATENT NO. : 11,236,289 B2  
APPLICATION NO. : 16/772516  
DATED : February 1, 2022  
INVENTOR(S) : Franco Papa and Renato Colognato Page 1 of 1

It is certified that error appears in the above-identified patent and that said Letters Patent is hereby corrected as shown below:

In the Claims

Claim 1, Column 12, Line 36, after the number 15, please add --%--.

Claim 5, Column 12, Line 53, after the words sesame oil, add --,--.

Claim 6, Column 12, Line 57, please delete "quant ty" and add --quantity--.

Claim 10, Column 13, Line 20, after the word in, please delete "the" and add --a--.

Claim 15, Column 14, Line 13, after the word of, please add --ozone--.

Signed and Sealed this  
Twenty-sixth Day of April, 2022

Katherine Kelly Vidal  
*Director of the United States Patent and Trademark Office*